(12) United States Patent
Bonnin et al.

(10) Patent No.: US 7,794,085 B2
(45) Date of Patent: Sep. 14, 2010

(54) METHOD AND DEVICE FOR DETERMINING THE EYE'S ROTATION CENTER

(76) Inventors: Thierry Bonnin, c/o Essilor International, 147, rue de Paris, 94227 Charenton-le-Pont (FR); Bruno Decreton, c/o Essilor International, 147, rue de Paris, 94227 Charenton-le-Pont (FR); Gildas Marin, c/o Essilor International, 147, rue de Paris, 94227 Charenton-le-Pont (FR); Cécile Petignaud, c/o Essilor International, 147, rue de Paris, 94227 Charenton-le-Pont (FR)

( * ) Notice: Subject to any disclaimer, the term of this patent is extended or adjusted under 35 U.S.C. 154(b) by 407 days.

(21) Appl. No.: 11/886,645

(22) PCT Filed: Mar. 10, 2006

(86) PCT No.: PCT/FR2006/050207

§ 371 (c)(1),
(2), (4) Date: Sep. 18, 2007

(87) PCT Pub. No.: WO2006/106248

PCT Pub. Date: Oct. 12, 2006

(65) Prior Publication Data
US 2009/0040460 A1    Feb. 12, 2009

(30) Foreign Application Priority Data
Apr. 8, 2005  (FR)  ................................. 05 50902

(51) Int. Cl.
*A61B 3/14* (2006.01)
*A61B 3/00* (2006.01)
(52) U.S. Cl. .................................... 351/209; 351/246
(58) Field of Classification Search ................ 351/209, 351/246
See application file for complete search history.

(56) References Cited

U.S. PATENT DOCUMENTS 6,580,448 B1  6/2003  Stuttler et al. ................. 348/46
2003/0169907 A1  9/2003  Edwards et al. ............. 382/118

OTHER PUBLICATIONS

International Search Report- Jun. 28, 2006.
XP009055840- American Journal of Optometry *and Archives of American Academy of Optometry*- Nov. 1962.

*Primary Examiner*—Jack Dinh
(74) *Attorney, Agent, or Firm*—Sofer & Haroun, LLP

(57) ABSTRACT

The invention relates to a device for determining the center of rotation of an eye of a person relative to a frame of reference associated with the person or with said person's eyeglasses, making it possible to determine the visual axis of the person along at least two non-parallel directions by viewing a target, and to define an optimum point of intersection of said axes as the center of rotation of the eye, at least two relative positions of said target and of the person's head being measured. In the invention, said target is constituted by a light source and is disposed at one end of a tubular support, with the other end being for disposing facing the person's eye, the support carrying a first position sensor, a second position sensor being for placing on the person's head.

8 Claims, 3 Drawing Sheets

METHOD AND DEVICE FOR DETERMINING THE EYE'S ROTATION CENTER

This application is a National Phase application of PCT/FR2006/050207, filed on Mar. 10, 2006, which in turn claims the benefit of priority from French Patent Application No. 05 50902, filed on Apr. 8, 2005, the entirety of which is incorporated herein by reference.

Field of the Invention:

The invention relates to a method and a device for determining the center of rotation of an eye.

The invention is preferably, but in non-limiting manner, intended for an ophthalmic application.

BACKGROUND OF THE INVENTION

When considering a person's vision, it is desired to describe that vision over the entire field of vision, both when looking straight ahead and when the eye gazes at different points in space. To do this, it is necessary to take account of the movement of the person's eyes, when said person gazes at different points of the field. The movement of the eye is commonly taken to be rotation about a particular point known as the Center of Rotation of the Eye (CRE).

The optical characteristics of an eye and lens system depend on the position of the CRE relative to the eyeglasses and it is normally considered that the CRE is placed on the primary gaze direction. Normally, using simple photography, it is possible to measure the distance between the rear face of the lens and the front face of the cornea along the primary gaze direction. The CRE is then positioned at a parameterized distance that may be equal to 15 millimeters (mm) behind the front face of the cornea.

More generally, the position of the CRE is measured relative to a point on the rear face or on the front face of the eyeglass lens, or a particular point on the person's face, relative to which the lens can be put in a known positioned.

These values normally used to determine the CRE are values that are theoretical, arbitrary, and standard.

Unfortunately, in practice, the position and the dimensions of the eye differ depending on the person, and, as a result, positioning the CRE by using such a theoretical value is approximate. More generally, the movements of the eye and thus the position of the CRE can be characterized by a function that is dependent on the gaze direction.

OBJECTS OF THE INVENTION

An object of the invention is to determine the position of the CRE by taking personalized measurements on the person concerned.

In the ophthalmic field, such personalized measurement determination makes it possible to develop ophthalmic lenses that are made to measure and that provide better performance.

In a more general field of application, the invention enables the CRE to be determined accurately. In particular, this is necessary in virtual-reality simulation applications in which the cameras need to be positioned accurately on the CRE for a correct 3D stereo rendition.

In theory, it is known to determine the center of rotation of an eye of a person relative to a frame of reference associated with the person, by determining the visual axis of the person along at least two non-parallel directions by viewing a target, and by defining an optimum point of intersection of said axes as the center of rotation of the eye.

However, that method poses the following technical problem.

For an accurate definition, it is necessary to hold the person's head stationary by means of a specific device of the chin-rest type. While moving the eye, even through a relatively small angle, a person tends to move the head by reflex, and any such movement leads to a definition that is necessarily approximate.

A device for determining the center of rotation of an eye of a person relative to a frame of reference associated with the person, making it possible to determine the visual axis of that person along at least two non-parallel directions by viewing a target, and to define an optimum point of intersection of said axes as the center of rotation of the eye, is described in U.S. Pat. No. 6,580,448, in which use is made of at least two relative positions of said target and of the person's head being measured.

However, the device proposed in that document is particularly complex in structure and to manipulate.

SUMMARY OF THE INVENTION

The invention proposes a device specifically for determining the center of rotation of an eye of a person, which device is very simple in structure and very easy to manipulate.

The invention solves this problem and to do this it proposes a device for determining the center of rotation of an eye of a person relative to a frame of reference associated with the person or with said person's eyeglasses, making it possible to determine the visual axis of the person along at least two non-parallel directions by viewing a target, and to define an optimum point of intersection of said axes as the center of rotation of the eye, at least two relative positions of said target and of the person's head being measured, wherein said target is constituted by a light source and is disposed at one end of a tubular support, with the other end being for disposing facing the person's eye, the support carrying a first position sensor, a second position sensor being for placing on the person's head.

By means of the invention, the person can be in a natural position or moving.

In a first variant embodiment, said target is a unidirectional point light source, preferably a laser, that ensures that the support is in alignment with the gaze direction when the person sees the target.

In a second variant embodiment, said target is any point light source, preferably a diode or a test chart, and the support includes a transparent second target, constituted by a transparent plate having a reticle or by a screen pierced by a hole, that is for placing facing the person's eye, and that ensures that the support is in alignment with the gaze direction when the person sees the two targets in alignment.

In a third variant, said support is a tube of small diameter that ensures alignment with the gaze direction when the person sees the target.

Advantageously, the three variants may be combined so as to improve alignment accuracy and/or make it easier to calibrate the appliance.

Advantageously, another transparent target, constituted by a transparent plate having a reticle or by a screen pierced by a hole, may be disposed between the first target and the middle of the support when said first target is a light source, so as to improve alignment accuracy by specifying the position of the target, and so as to make it easier to calibrate the appliance.

The device of the invention may also include a screen that is stationary relative to the person's head and disposed in front of the person's eye, and that is provided with translucent point zones that correspond to said directions.

The screen may be fastened onto an eyeglass frame or a helmet.

Advantageously, the translucent point zones, which may merely be holes, have a diameter that is smaller than the natural diameter of the pupil of the person's eye, and that preferably lies in the range 0.5 mm to 2 mm.

The invention also provides a method of determining the center of rotation by means of a device as defined above, at least two relative positions of said target and of the person's head being measured.

In a first variant implementation, the optimum point of intersection is defined by defining a surface that is perpendicular to each of said visual axes, and then by defining the best focus for said surface, the best focus being defined as the center of rotation of the eye.

In a second variant implementation, the optimum point of intersection is defined by defining, for each pair of visual axes, the point that is equidistant from said two axes and that is at the minimum distance from said two axes, and then by defining the barycenter of said points, the barycenter being defined as the center of rotation of the eye.

In a third variant implementation, the optimum point of intersection is defined by defining, for each pair of visual axes, the point that is equidistant from said two axes and that is at the minimum distance from said two axes, and then by defining a sphere of minimum radius that contains said points, the center of said sphere being defined as the center of rotation of the eye.

The method is optimized and makes it possible to determine the CRE to within an error of less than one millimeter.

Advantageously, said identified directions are substantially symmetrical about the eye gazing straight ahead.

BRIEF DESCRIPTION OF THE DRAWINGS

The invention is described in greater detail below with reference to the figures, which show a preferred embodiment only of the invention.

MORE DETAILED DESCRIPTION

Figure 1:
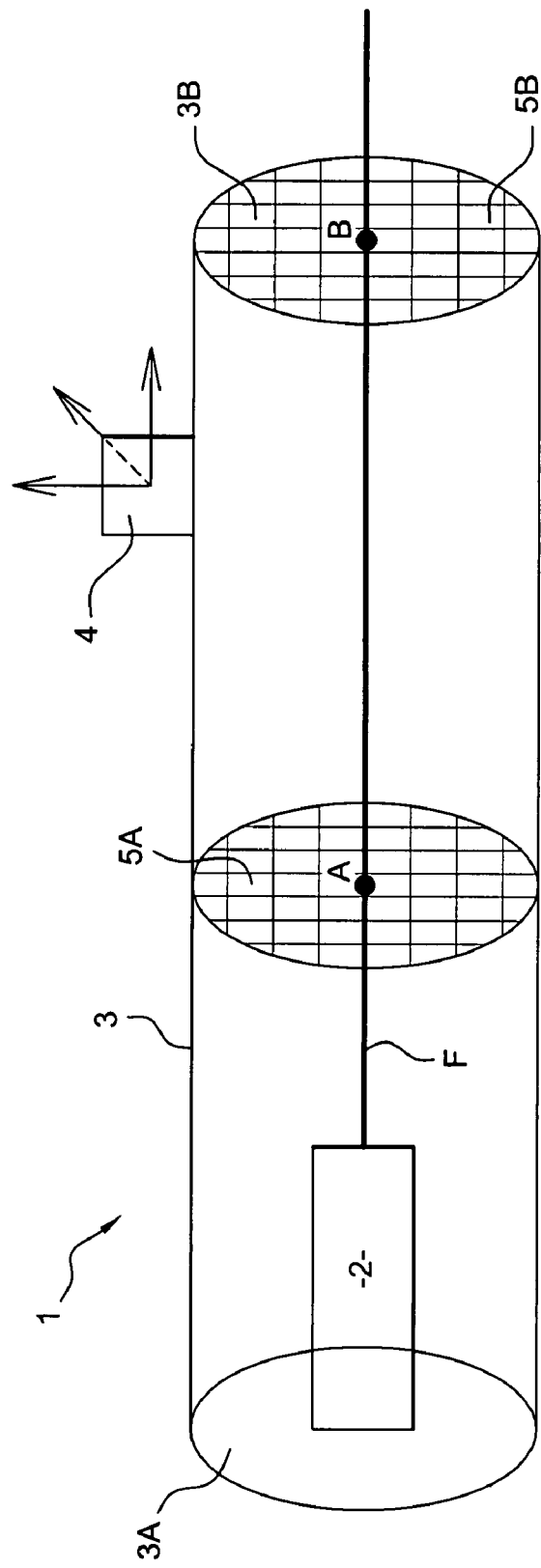
FIG. 1 is a diagrammatic view of a device of the invention, constituting a first variant embodiment.

As shown in FIG. 1, a device 1 of the invention includes a target, preferably constituted by a light source 2, that is disposed at one end 3A of a support 3, e.g. formed by a cylindrical duct or tube, with its other end 3B being for placing facing the person's eye.

Two transparent plates 5A, 5B carrying reticles are disposed in the tube, one of which 5A is preferably disposed in the proximity of the light source 2, e.g. mid-way along the tube, and the other of which 5 B is preferably disposed at the open end 3B of the tube. The plates can be replaced by screens that are pierced by respective central holes.

The plate 5B disposed at the open end 3B of the tube is optional when the light source 2 is a unidirectional point source, such as a laser for example. The plate 5A disposed in the proximity of the light source 2 is always optional.

Figure 2:
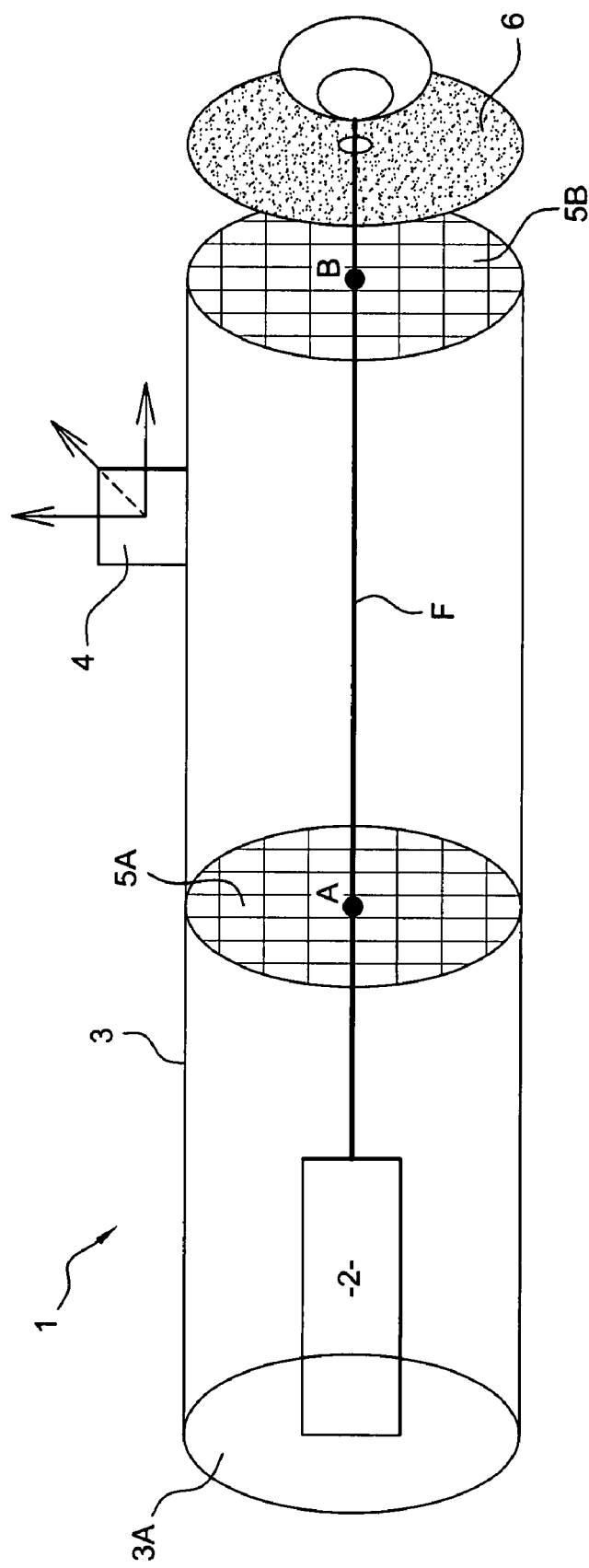
FIG. 2 is a diagrammatic view of a device of the invention, constituting a second variant embodiment.

The FIG. 1 device can advantageously be completed by a pierced screen 6 that is disposed in front of the person's eye, and that is stationary relative to the head by being fastened onto the frame of eyeglasses or onto a helmet, as shown in the FIG. 2 variant.

The longitudinal positions of the elements along the support 3 can be adjusted in order to be adapted to the person's sight.

The support 3 carries a first position sensor 4 that, on being calibrated, makes it possible to know the direction of the light beam F relative to the position of the sensor on the support 3, e.g. by detecting points A and B.

A fine light beam F is thus defined, thereby making it possible to identify a direction corresponding to a visual axis.

Figure 3:
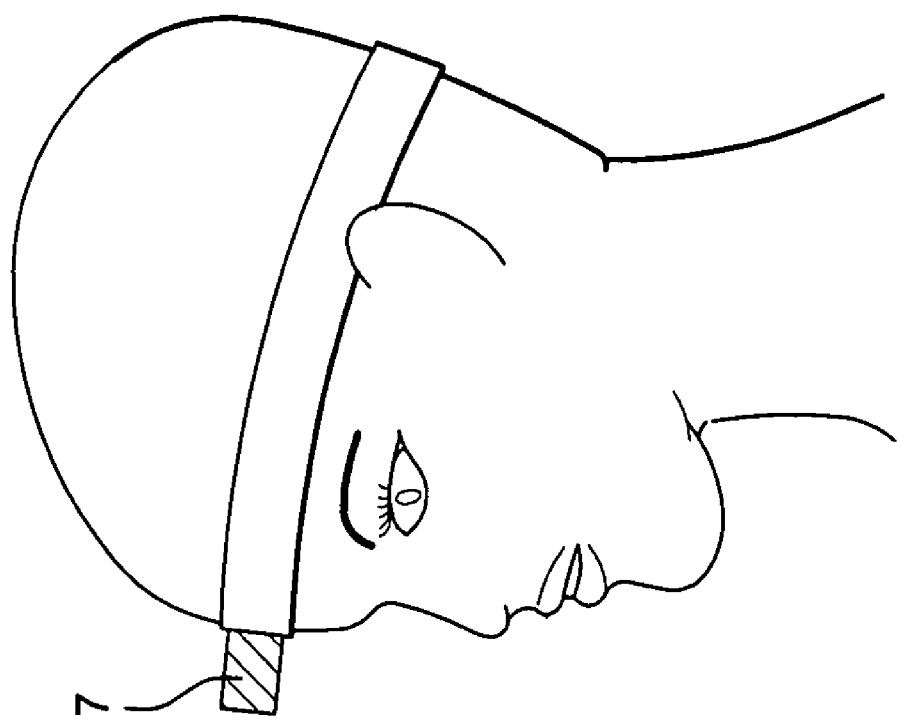
FIG. 3 is a view of the device of the invention worn by a person.
Figure 3:
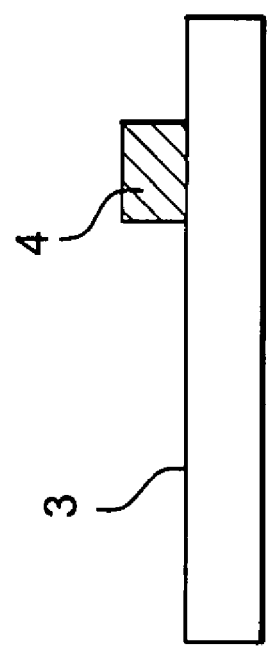

As shown diagrammatically in FIG. 3, the device includes a second position sensor 7 for being worn on the person's head, which head is likely to turn. Stationary relative to the head, e.g. secured by a headband, the sensor 7 makes it possible to know the position of the head at all times. By way of example, both sensors can be "Fastrak" sensors from the supplier Polhemus.

The support 3 and its light beam F, and also the person's head need to be calibrated.

Such calibrations can be performed as follows.

Calibrating the support makes it possible to calculate the transformation, making it possible to pass from the frame of reference of the first sensor 4 to a frame of reference associated with the direction of the axis F.

One method is as follows.

The axis F is embodied by a light beam coming from the target 2 if said target is a light source, or by the target 2 and the transparent plates with reticles 5B and optionally 5A. A movable point marker is used to point out the position of the target 2 embodying one of the ends of the axis F. The position of the other end of the axis F, as embodied either by the beam intersecting the other end of the support or by the plate 5B, is determined in the same way. Advantageously, it is possible to determine the position of the plate 5A in addition to, or instead of, that of the target 2, in particular when the target 2 is a light source having a position that is more difficult to identify. An electronic system supplies the coordinates of said two points, expressed in one particular frame of reference. The system simultaneously supplies the axes of the frame of reference associated with the first sensor 4 secured to the support. The support 3 does not need to be stationary during the measurements, since it is the difference in position between the sensor 4 and the movable point marker that is measured at all times.

A simple calculation makes it possible to pass from the frame of reference of the first sensor 4 to the direction of the axis F.

Calibrating the head makes it possible to calculate the transformation, making it possible to pass from the frame of reference associated with the second sensor 7 on the head to a particular and known frame of reference of said head.

One method is as follows.

A movable point marker is used to point out the particular point to be positioned. An electronic system supplies the coordinates of said point, expressed in a particular frame of reference. The system simultaneously supplies the axes of the frame of reference associated with the second sensor 7 secured to the head. The head does not need to be stationary during the measurements, since it is the difference in position between the sensor 7 and the movable point marker that is measured at all times.

The movable point marker used above for calibration can be a so-called "Stylus" from the supplier Polhemus.

The particular points and the axes needed can advantageously be made up of:

the root of the nose: the origin of the frame of reference;
the axis that joins the center of the right pupil and the center of the left pupil; $1^{st}$ axis;
the vertical axis: $2^{nd}$ axis; and
the $3^{rd}$ axis is calculated so as to form a right-handed Cartesian system.

The particular point can also advantageously be the center of the rear face of the lens so as to deduce the lens-to-CRE distance directly from the measurement of the position of the CRE.

Once the points and the axes have been identified on the person, simple calculation suffices to change the frame of reference, making it possible to pass at any time from the frame of reference associated with the second sensor 7 to the frame of reference associated with the head.

After calibration has been performed, the device can be used as follows.

The person removes the eyeglasses and takes hold of the support 3. The person positions the support in front of an eye and moves said eye until the target 2 and any additional targets formed by the aligned plates or screens 5A and 5B can be seen. At this moment, the axis of the eye coincides with the direction of the axis F.

The sensors 4 and 7 and associated software then make it possible to record the direction of the visual axis and the position of the head. Software then calculates the direction of the visual axis in the frame of reference associated with the head.

The person is asked to turn the tube in any direction. The person then moves the eye, and, if so desired, the head, so as to align the targets once again or so as to view the light source.

Another direction of the visual axis and position of the head are then recorded.

This operation is performed at least twice, so as to make it possible to determine two visual axes.

The accuracy with which the CRE is positioned depends, amongst other things, on the number of directions that are measured in three dimensions, and on the angular offset between the various directions.

By way of example, in order to keep manipulation comfortable for the person, it is possible to process about 10 data acquisitions, separated by 20° in all directions.

For example, it is possible to use the following nine directions:
1/gaze straight ahead;
2/up (about 200);
3/up (about 400);
4/down (about –200);
5/down (about –40°);
6/right (about 200);
7/right (about 400);
8/left (about –20°); and
9/left (about –40°).

It is also possible to use the following nine other directions:
1/gaze straight ahead;
2/up (about 40°);
3/down (about –40°);
4/right (about 40°);
5/left (about –400);
6/up (about 40°) and right (about 40°);
7/up (about 400) and left (about –40°);
8/down (about –40°) and right (about 40°); and
9/down (about –40°) and left (about –40°).

It is advantageous for the identified visual axes to be approximately symmetrical about the straight-ahead gaze axis.

Once the visual axis directions and the head positions have been collected, manipulation comes to an end.

For all of the acquisitions, the software calculates the direction of the visual axis in the frame of reference associated with the head.

Using an appropriate algorithm, the software then calculates the best position for the CRE on the basis of all of the directions.

In a first variant implementation, the optimum point of intersection is defined by defining a surface that is perpendicular to each of said visual axes, and then by defining the best focus for said surface, the best focus being defined as the center of rotation of the eye.

In a second variant implementation, the optimum point of intersection is defined by defining, for each pair of visual axes, the point that is equidistant from said two axes and that is at the minimum distance from said two axes, and then by defining the barycenter of said points, the barycenter being defined as the center of rotation of the eye.

In a third variant implementation, the optimum point of intersection is defined by defining, for each pair of visual axes, the point that is equidistant from said two axes and that is at the minimum distance from said two axes, and then by defining a sphere of minimum radius that contains said points, the center of said sphere being defined as the center of rotation of the eye.

The device of the invention can be used in various ways in order to acquire the lines necessary for determining the center of rotation of the eye, the above-described mode of use being only one example.

In a first mode of use, the person can adopt any posture and hold the tube in one hand.

The advantage of this first mode of use is the fact that the person is free to move both the head and eye, and remains in natural positions. Nevertheless, the experimenter must ensure that the person changes the direction of gaze properly. This makes it possible to fit in with a person's habitual head and eye movements.

In a second mode of use, a screen 6 that is pierced in certain places is placed in front of the person's eyes with the purpose of forcing the person to look in certain directions. In this event, the device of the invention also comprises this screen disposed in front of the person's eye, and provided with translucent point zones that correspond to said directions.

The advantage of this second mode of use is to ensure that the directions of gaze are properly distributed in three dimensions, thereby making it possible to control the manipulation properly, and to calculate the distribution of the directions of gaze so as to obtain the best accuracy. Another advantage of this mode of use is that even though the size of the subject's pupil is of no consequence, pupil size can limit accuracy in positioning the direction of gaze, with this being achieved by using holes of a desired size, e.g. of diameter lying in the range 0.5 mm to 2 mm.

In a third mode of use, the tube is secured to a measurement bench, thereby providing more accurate alignment. It is also possible to use a pierced screen.

The advantage of this third mode of use is in making it possible to provide more accurate and stable alignment by avoiding the small amount of shaking that is associated with the tube being held in the hand.

For a given eye, it is also possible to determine a plurality of positions of the CRE that correspond to a plurality of pairs of visual axes. The position of the CRE is thus a function of pairs of visual axes.

For example, the straight-ahead gaze axis is taken as an axis of reference and a plurality of visual axes that are symmetrical about the straight-ahead gaze axis are determined. A position for the CRE is determined for each axis pair (straight-ahead, other visual axis).

Such a set of positions for the CRE can be used in the ophthalmic field.

What is claimed is:

1. A device for determining the center of rotation of an eye of a person relative to a frame of reference associated with the person or with said person's eyeglasses, making it possible to determine the visual axis of the person along at least two non-parallel directions by viewing a target, and to define an optimum point of intersection of said axes as the center of rotation of the eye, at least two relative positions of said target and of the person's head being measured, said device comprising:

a target including a light source disposed at one end of a tubular support, only one tube of small diameter, said tubular support being configured to be placed apart from the person's head, with the other end of said target being for disposing facing the person's eye; and a support carrying a first position sensor, a second position sensor being for placing on the person's head.

2. A device according to claim 1, also including a transparent second target that is for disposing facing the person's eye.

3. A device according to claim 1, also including another transparent target that is for disposing between said light source and the middle of the support.

4. A device according to claim 1, also including a screen that is stationary relative to the person's head and disposed in front of the person's eye, and that is provided with translucent point zones that correspond to said directions.

5. A method of determining the center of rotation by means of a device according to claim 1, said method comprising the step of:

measuring at least two relative positions of said target and of the person's head, wherein the optimum point of intersection is defined by defining a surface that is perpendicular to each of said visual axes, and then by defining the best focus for said surface, the best focus being defined as the center of rotation of the eye.

6. A method of determining the center of rotation by means of a device according to claim 1, said method comprising the step of:

measuring at least two relative positions of said target and of the person's head, wherein the optimum point of intersection is defined by defining, for each pair of visual axes, the point that is equidistant from said two axes and that is at the minimum distance from said two axes, and then by defining the barycenter of said points, the barycenter being defined as the center of rotation of the eye.

7. A method of determining the center of rotation by means of a device according to claim 1, said method comprising the step of:

measuring at least two relative positions of said target and of the person's head, wherein the optimum point of intersection is defined by defining, for each pair of visual axes, the point that is equidistant from said two axes and that is at the minimum distance from said two axes, and then by defining a sphere of minimum radius that contains said points, the center of said sphere being defined as the center of rotation of the eye.

8. A method according to claim 5, wherein said identified directions are substantially symmetrical about the eye gazing straight ahead.

* * * * *